(12) United States Patent
Neculaes et al.

(10) Patent No.: US 9,078,862 B2
(45) Date of Patent: Jul. 14, 2015

(54) PLATELET ACTIVATION USING LONG ELECTRIC FIELD PULSES

(71) Applicant: General Electric Company, Schenectady, NY (US)

(72) Inventors: Vasile Bogdan Neculaes, Niskayuna, NY (US); Antonio Caiafa, Albany, NY (US); Brian Duh-Lan Lee, Rexford, NY (US); Nicole Evelyn LaPlante, Amsterdam, NY (US); Andrew Soliz Torres, Niskayuna, NY (US); Allen Lawrence Garner, West Lafayetter, IN (US)

(73) Assignee: General Electric Company, Niskayuna, NY (US)

( * ) Notice: Subject to any disclaimer, the term of this patent is extended or adjusted under 35 U.S.C. 154(b) by 121 days.

(21) Appl. No.: 13/912,050

(22) Filed: Jun. 6, 2013

(65) Prior Publication Data

US 2014/0363412 A1 Dec. 11, 2014

(51) Int. Cl.

| | |
|---|---|
| *A61K 35/19* | (2015.01) |
| *C12N 13/00* | (2006.01) |
| *A61K 41/00* | (2006.01) |
| *C12N 5/078* | (2010.01) |
| *A61N 1/00* | (2006.01) |

(52) U.S. Cl.
CPC ............... *A61K 35/19* (2013.01); *A61K 41/00* (2013.01); *A61N 1/00* (2013.01); *C12N 5/0644* (2013.01); *C12N 13/00* (2013.01)

(58) Field of Classification Search
None
See application file for complete search history.

(56) References Cited

U.S. PATENT DOCUMENTS

| | | | |
|---|---|---|---|
| 4,935,223 A | 6/1990 | Phillips | |
| 5,773,228 A | 6/1998 | Reed et al. | |
| 5,840,499 A | 11/1998 | Brass et al. | |
| 6,326,177 B1 * | 12/2001 | Schoenbach et al. | 435/173.7 |
| 6,432,119 B1 | 8/2002 | Saadat | |
| 6,773,669 B1 | 8/2004 | Holaday et al. | |
| 7,029,916 B2 | 4/2006 | Dzekunov et al. | |
| 7,141,425 B2 | 11/2006 | Dzekunov et al. | |
| 7,186,559 B2 | 3/2007 | Dzekunov et al. | |
| 7,565,201 B2 | 7/2009 | Blackmore et al. | |
| 7,771,660 B2 | 8/2010 | Gabriel | |
| 7,875,296 B2 | 1/2011 | Binette et al. | |
| 8,000,813 B2 | 8/2011 | Schoenbach et al. | |
| 2001/0001064 A1 | 5/2001 | Holaday | |
| 2003/0198687 A1 * | 10/2003 | Bennett et al. | 424/532 |
| 2005/0048651 A1 * | 3/2005 | Ryttsen et al. | 435/459 |
| 2006/0269531 A1 * | 11/2006 | Beebe et al. | 424/93.21 |
| 2008/0103529 A1 | 5/2008 | Schoenbach et al. | |
| 2010/0280513 A1 | 11/2010 | Juergen et al. | |
| 2011/0318319 A1 | 12/2011 | Hargrave et al. | |
| 2012/0035511 A1 | 2/2012 | Schoenbach et al. | |
| 2012/0088842 A1 | 4/2012 | Dzekunov | |
| 2012/0109263 A1 | 5/2012 | Kolb et al. | |

OTHER PUBLICATIONS

Ok, Seung-Bok, "Design of a High-Efficiency 40-kV, 150-A, 3-kHz Solid-State Pulsed Power Modulator," IEE Transactions on Plasma Science, vol. 40, No. 10, Oct. 2012, pp. 2569-2577.

Xiao, S., "Pulsed Power for Wound Healing," 2008, pp. 69-72, IEEE International Power Modulator & High Voltage Conference, Proceedings of the 2008.

Lonza, "Amaxa Nucleofector 2b Manual for Research Use Only," 2011, pp. 1-20.

\* cited by examiner

*Primary Examiner* — Allison Fox
*Assistant Examiner* — Susan E Fernandez
(74) *Attorney, Agent, or Firm* — Eileen B. Gallagher

(57) ABSTRACT

Embodiments of the disclosure relate to platelet activation and/or aggregation using electric pulses. In one embodiment, a platelet-containing sample is exposed to electric pulses. At least one of the electric pulses has a duration greater than 1 microsecond and a field strength below 50 kV/cm. In another embodiment, the electric pulses may be designed with particular field strengths and durations.

13 Claims, 15 Drawing Sheets

PLATELET ACTIVATION USING LONG ELECTRIC FIELD PULSES

BACKGROUND

The subject matter disclosed herein relates to platelet activation using long field electric pulses.

Application of activated platelets to blood may enhance physiological wound repair processes. For example, in one technique, platelet rich plasma is obtained from whole blood using various separation techniques, such as centrifugation. In turn, the platelet rich plasma may be activated by treatment with certain activating compounds, such as thrombin and calcium chloride, to generate activated platelets and/or a platelet gel that may be applied to a wound to promote hemostasis and/or healing.

BRIEF DESCRIPTION

In one embodiment, a method is provided that includes exposing a platelet-containing sample to one or more electric pulses, wherein at least one pulse has a duration greater than 1 microsecond a field strength of less than 50 kV/cm; and applying the platelet-containing sample to a patient.

In another embodiment, a method is provided that includes receiving a user input related to a platelet-containing sample; and applying electric pulses to the platelet-containing sample based on the user input, wherein at least one pulse has a duration greater than 1 microsecond and a field strength of less than 50 kV/cm.

In yet another embodiment, a system for activating platelets includes a pulse generator configured to generate one or more electric pulses. The system also includes a sample holding area coupled to the pulse generator and positioned to expose a sample to electric pulses; and a processor coupled to the pulse generator and configured to control pulse generator, wherein the processor is configured to: receive a user input related to a sample; select a protocol stored a memory; and drive the pulse generator to generate electric pulses, wherein at least one pulse has a duration greater than 1 microsecond and a field strength of less than 50 kV/cm.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
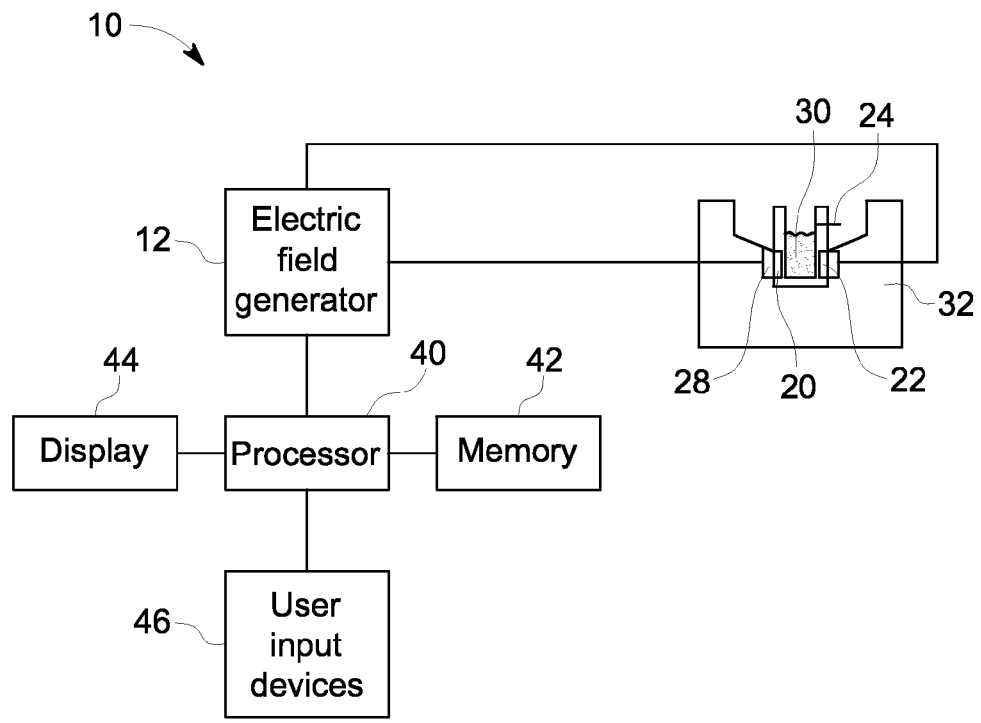
FIG. 1 is a block diagram illustrating an embodiment of a platelet activation system.

Platelet activation and/or aggregation may be used to treat wounds wounds in vivo and/or ex vivo. In one example, a platelet activating compound, such as thrombin or collagen, may be applied directly to a wound to promote in vivo platelet activation. In another approach, platelet rich plasma may be activated ex vivo using calcium chloride combined with thrombin, or collagen to form a platelet gel that may be applied to the wound. Provided herein are techniques for activating platelets by applying electric pulses of various durations and intensities. In one embodiment, the technique may be used to activate platelets in conjunction with devices configured to apply the appropriate electric pulses.

Researchers have previously used electric fields to affect cells. For example, in transfection, electric fields are used to porate cell membranes to facilitate DNA plasmid entry into the cell. Such techniques typically involve applying electric pulses with sufficient strength and duration to permeabilize the cell membrane while maintaining viability. Once the cell membrane is rendered "leaky," DNA in a surrounding buffer solution passes into the cell. Such techniques allow researchers to add foreign DNA to various cell types, including bacterial, mammalian, and yeast cells. Typically, the transfected cells are provided in a specialized buffer that promotes passage of DNA in the cells. Therefore, the workflow for electroporation involves suspending the cells of interest in a specific buffer, adding the DNA in the buffer, exposing the complex of cells-buffer-DNA to electric pulses to promote uptake of DNA into the cells. Some cell types require specific buffers for transfection. Typically, transfection using electroporation involves suspending cells in a specially designed buffer with specific properties, such as pH and low conductivity.

While electroporation targets the outer cell membrane to facilitate DNA transport, certain platelet aggregation techniques apply pulsed electric fields to induce intracellular and extracellular calcium transport by applying submicrosecond electric pulses of high field strength to platelets. Specifically, nanosecond electric pulses with field intensities up to 350 kV/cm, much higher than traditional electroporation, target the small organelles within platelets containing calcium stores. These nanosecond pulses may induce different effects than traditional electroporation, including manipulation of intracellular structures, such as granules, mitochondria, and the endoplasmic reticulum. While providing unique capabilities, nanosecond pulses possess several practical disadvantages for commercialization: instruments to generate high voltage nanosecond pulses are more complex and expensive than longer duration, lower amplitude pulses; the higher electric fields can trigger arcing inside the instrument and in the cuvette where the biological samples are located; and generating square pulses of short duration requires higher dV/dt (high voltage variation in a short amount of time) that may damage the instrument and/or degrade reliability.

In contrast to implementations of submicrosecond pulses for platelet activation, the disclosed embodiments activate platelets with electric pulses in excess of 1 microsecond and, in certain embodiments, in excess of 100 microseconds. Because it is easier to generate longer electrical pulses with lower field strength than submicrosecond pulses of higher field strength, the disclosed embodiments may be implemented more easily with simpler and and more reliable circuitry; for example, generating submicrosecond pulses may require complex pulse compression techniques. Further, the disclosed embodiments achieve growth factor release from organelles, such as alpha granules with diameters of hundreds of nanometers, within platelets that are a few microns in diameter without using submicrosecond electric pulses.

Applying much longer pulses of microseconds or tens of microseconds with lower field strengths reduces the risk of arcing in the cuvette while still activating the platelets. Typically, submicrosecond pulses require higher electric fields than longer pulses to induce comparable biological effects. These higher electric fields at nanosecond duration create a favorable environment for arcing in the cuvette. By extending the pulse duration allows the square shape to be achieved using smaller dV/dt, which dramatically reduces EMI (electromagnetic interference) in the instrument used for platelet activation. High EMI would pose significant challenges for an instrument designed for nanosecond pulse generation. In addition, the disclosed embodiments use longer pulses that may include variable or shaped characteristics. For example, a higher amplitude component of the pulse may target the intracellular structures within the platelets, while a lower amplitude component of the pulse may target the cell membrane of the platelets.

Another advantage of the disclosed techniques is that the samples exposed to the pulsed electric fields will be processed using instruments designed specifically for the electrical load represented by platelet rich plasma. Typical electroporation instruments are designed for electrical loads that are not very conductive—which means lower current and lower power requirements. Electrical loads, such as platelet rich plasma, have high conductivity, lower resistance for instruments that require high current, high power capabilities. In particular, in contrast to other techniques, the electrical parameters of the device (electric field strength, current, power delivered to the sample) are tuned to the parameters of the sample so that a full cuvette, when exposed to the appropriate pulsed electric field, can deliver the pulses to the sample without damaging the sample or the device. Further, in contrast to electroporation techniques in which the samples are first suspended in a low conductivity buffer, the disclosed techniques do not require a specific buffer. For example, platelets may be part of the platelet rich plasma, which is created by putting the whole blood drawn from a patient in a platelet separation device, such as a centrifuge. Platelet rich plasma is not designed to have special properties with regard to pH or low electrical conductivity, which are important characteristics for the low conductivity buffers used in electroporation; actually platelet rich plasma being separated from whole blood has higher electrical conductivity compared to typical low conductivity specially designed electroporation buffers. This disclosed techniques, as noted, involve power specification that permit samples to be filled at least ⅔ full, or at least ½ full within a sample cuvette. This is in contrast to other techniques, for which such full cuvettes at the typical power loads would lead to arcing and sample degradation. Accordingly, the disclosed techniques may lead to higher throughput and more efficient sample processing.

FIG. 1 shows schematically a system 10 for platelet activation. The system includes an electric field generator 12 and electrode sets (or arrays of electrodes) 20 and 22. In the depicted embodiment, the electrodes 20 and 22 are spaced apart on opposing walls of a cuvette 24. That is, the electrodes are disposed on the cuvette 24 and are coupled to the pulse generator via contacts 28. The cuvette 24 is configured to hold a sample 30 that contains platelets. In certain embodiments, the cuvette 24 is disposable and is removable from the sample holder 32. Accordingly, insertion of the cuvette 24 and contact of the electrodes 20 and 22 with the contacts 28 allows the pulse generator to produce an electric pulse, and the sample 30 within the cuvette 24 is exposed to the pulses. The cuvette 24 may be any suitable structure configured to hold the sample 30 and conduct the electric pulses. The cuvette 24 holds the electrodes 20 and 22 spaced apart from one another, and the gap between these electrodes 20 and 22 may influence the strength of the electric field. In one embodiment, the cuvette is configured to have a 1 cm gap between the electrodes 20 and 22. The electric field strength is the ratio of the applied voltage and the cuvette gap distance. Exposing a 1 cm cuvette to 1 kV gives a field strength of 1 kV/cm. For implementations involving smaller cuvettes, such as a 0.5 cm cuvette, 500V may yield a 1 kV/cm field strength. In another embodiment, the electric field strength is less than approximately 50 kV/cm.

In certain embodiments, the system may include suitable control and input circuitry and may be implemented in a dedicated housing or may be coupled to a computer. The system 10 may include a processor 40 that control the electric field generator 12. Additional components of the system 10 may include a memory 42 storing instructions that executed by the processor 40. Such instructions may include protocols and/or parameters for the electric field generated by the pulse generator 12. The processor 40 may include, for example, general-purpose single- or multi-chip microprocessors. In addition, the processor 40 may be any conventional special purpose processor, such as an application-specific processor or circuitry. The memory 42 may be a mass storage device, a FLASH memory device, removable memory, etc. In addition, a display 44 may provide indications to an operator related to the operation of the system 10. The system 10 includes a user input device 46 (e.g., a keyboard, mouse, touchscreen, trackball, hand held device such as PDA or smart phone or any combination thereof) for activating the pulse generator 12 and/or selecting appropriate parameters.

In the depicted embodiment, platelet activation is performed ex vivo. For example, the sample may be a blood product that has been removed from the body and processed to enrich the platelet concentration (e.g., platelet rich plasma). In other embodiments, the disclosed techniques may be in vivo. Accordingly, the system 10 may be implemented as a wand or other handheld device with spaced electrodes that deliver an electric field in or on a patient.

It is envisioned that the platelet activation system 10 as provided herein may be implemented as a single-purpose device for platelet activation or as a multi-purpose device that may be used for additional electric field exposure applications, such as electroporation. Further, the system 10 may be configured to generate an electric field according to one or more protocols. The protocols may be generated by user inputs and/or may be stored in the memory 42 to be selected by the user. In one embodiment, the system 10 may operate without any user input to the activation protocol other than an input to start activation once the sample 30 is loaded. In such an embodiment, the pulse generator 12 may operate under control of the processor 40 to operate a single protocol with predetermined electric field strength, pulse length, and/or total exposure time. Such a protocol may be determined by empirical studies. In other embodiments, the system 10 may be configured to receive a user input related to the electric field strength, pulse length, and/or total exposure time. Further, the system 10 may be configured to generate a particular pulse shape or to generate a series of pulses that may differ from one another according to a user input and/or a stored protocol setting.

Figure 2:
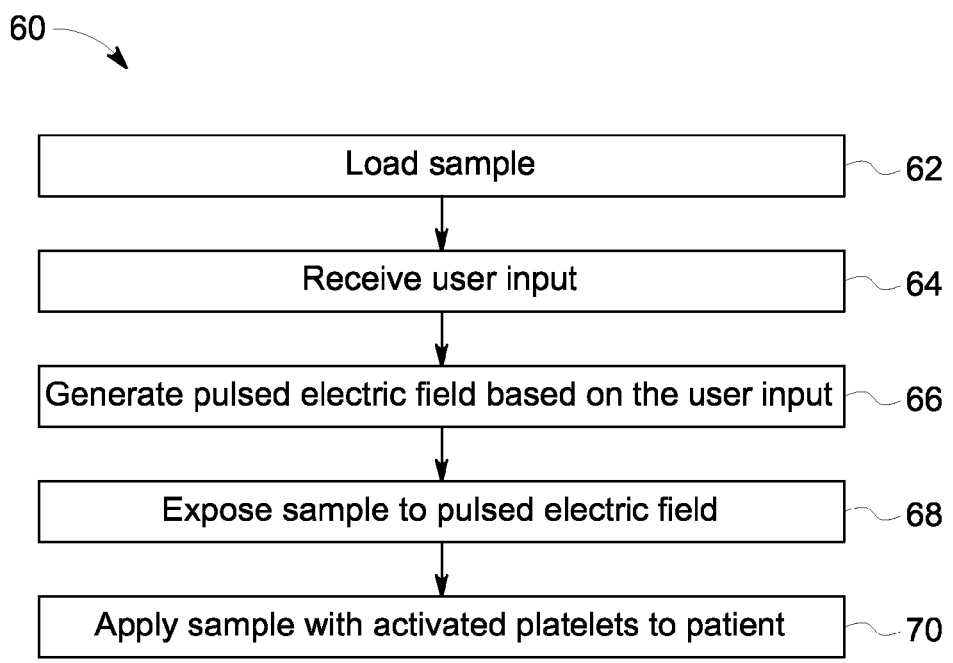
FIG. 2 is a is a flow diagram of a platelet activation technique according to an embodiment of the present disclosure.

FIG. 2 is a flow diagram showing a method 60 of platelet aggregation that may be performed in conjunction with the system 10. It should be understood that certain steps of the method 60 may be performed by an operator while other steps of the method may be performed by the system 10. At step 62, a suitable sample 30, such as platelet rich plasma is loaded into the holder 32. At step 64, a user input relating to electric field parameters is received by the system 10. Once the system 10 has received the user input, the pulse generator generates an electric field according to the input at step 66, and the sample is exposed to the electric field at step 68. Once the electric field is applied to the sample 30, the platelets are activated and the sample 30 may be applied to a patient at step 70. In one embodiment, the activated platelets are in the form of a gel and may be applied via syringe to a wound. In particular embodiments, the sample is derived from autologous blood.

It should be understood that any of the disclosed platelet activation parameters may be used either alone or in combination with one another. For example, the disclosed electric field strengths, pulse shapes, pulse lengths, and/or pulse patterns may be used alone or in combination with one another. In a specific implementation, the input relates to an electric field strength and duration. For example, according to certain embodiments of the disclosure, the applied voltage may be less than 10 kV or less than 50 kV. In specific embodiments, the applied voltage is 5000V or less, 1000V or less, or 500V or less. In addition, the pulse length may be greater than 1 microsecond, greater than 5 microseconds, greater than 10 microseconds, or 100 microseconds or greater. In one embodiment, the pulse length is 100 microseconds.

Figure 3:
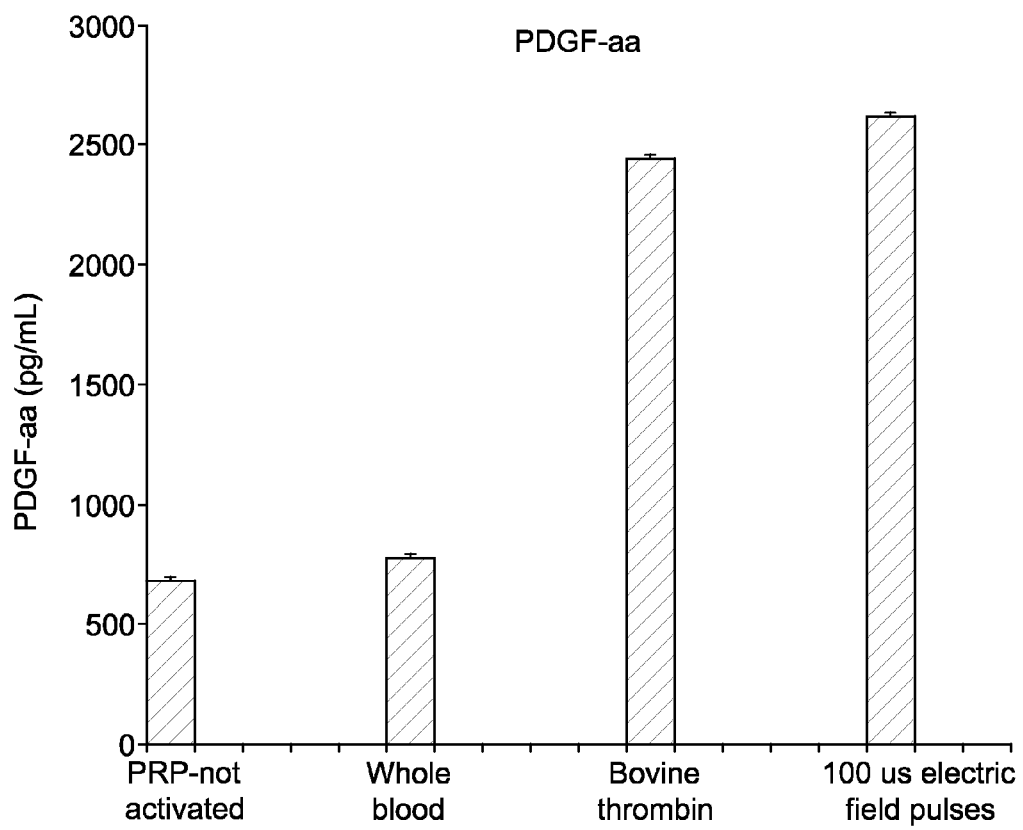
FIG. 3 is a graph showing platelet-derived growth factor release as a marker for platelet activation for thrombin activation relative to extended duration electric pulses.

FIGS. 3-7 illustrate the results of platelet aggregation testing performed to assess various platelet aggregation markers, such as release of growth factors associated with platelet activation. FIG. 3 is a graph in which the y-axis shows concentration of platelet-derived growth factor and the x-axis shows various tested samples. A control of platelet rich plasma that was not activated is shown relative to a control of whole blood. Activated platelets that were activated with exposure to bovine thrombin are graphed relative to platelets activated with long pulses of 100 microseconds, 900V amplitude, and a 7 microsecond rise time. The extended duration electric pulse technique yielded release of platelet-derived growth factor, and greater release relative to the thrombin activation sample.

Figure 4:
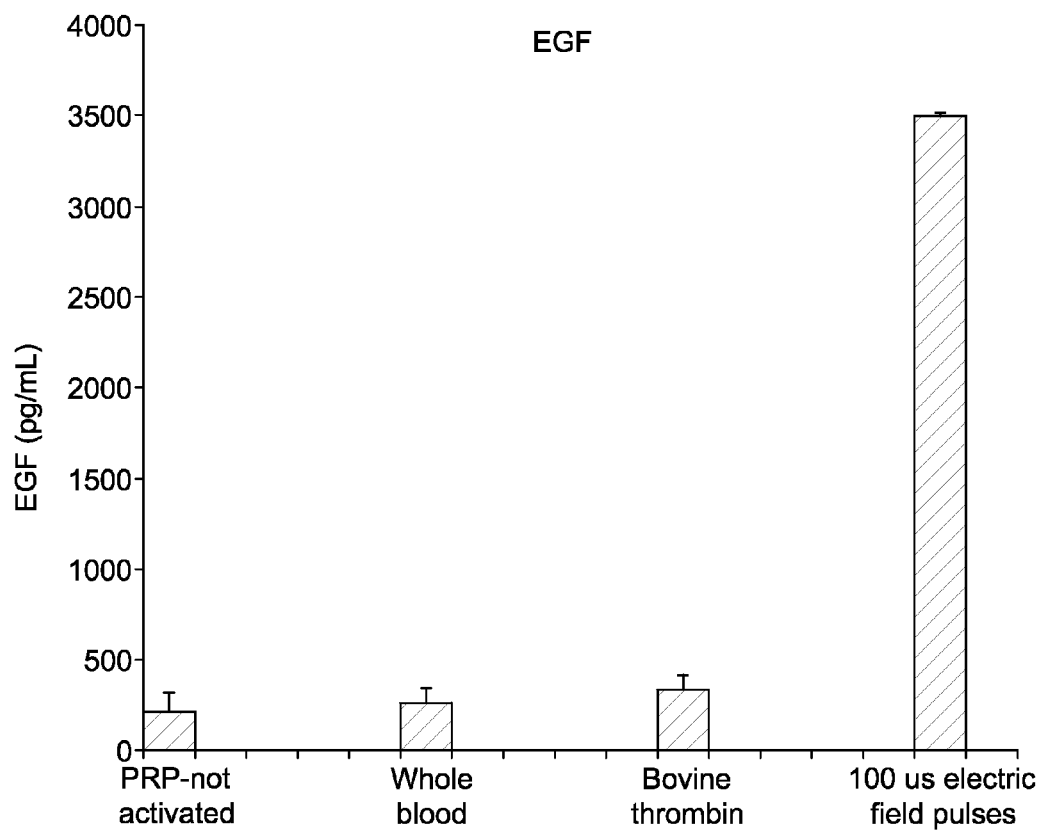
FIG. 4 is a graph showing epidermal growth factor release as a marker for platelet activation for thrombin activation relative to extended duration electric pulses.

FIG. 4 is a graph showing epidermal growth factor release. In this experiment, the sample exposed to long electric pulses of 100 microseconds, 900V, and a 7 microsecond rise time showed significantly more evidence of platelet activation relative the sample exposed to bovine thrombin.

Figure 5:
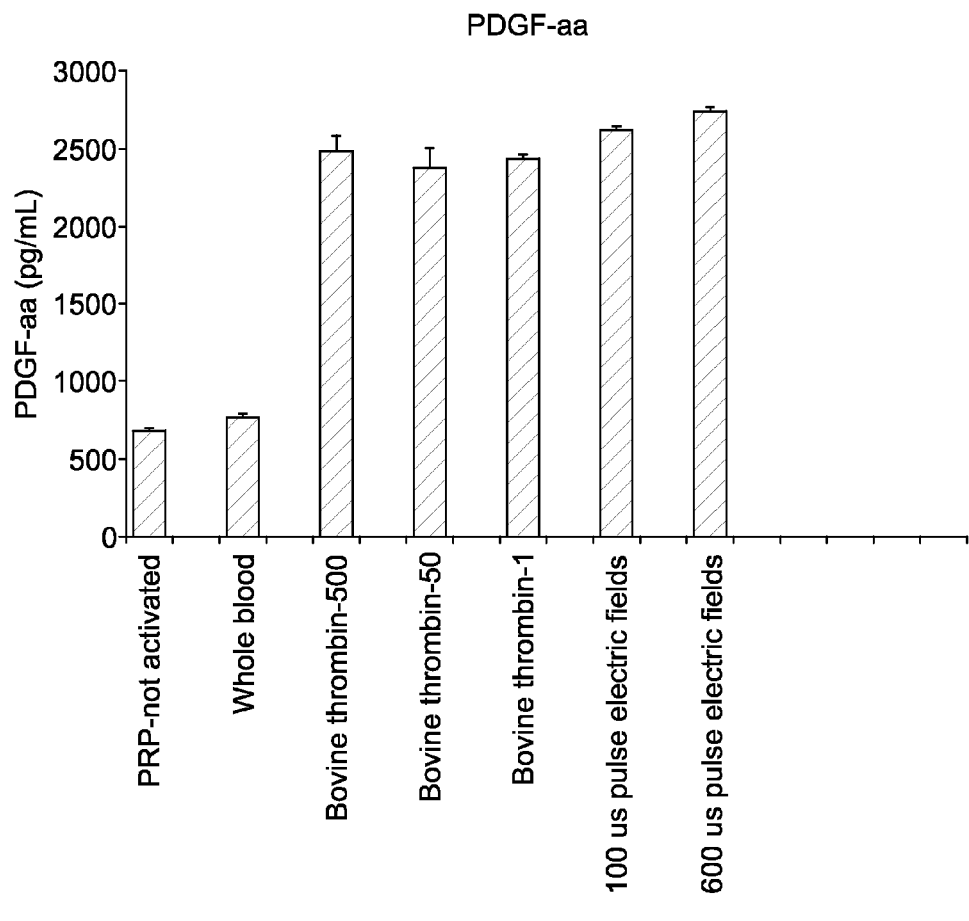
FIG. 5 is a graph showing platelet-derived growth factor release as a marker for platelet activation using various techniques relative to extended duration electric pulses.

Similar results were achieved when testing long electric pulses against additional thrombin-treated samples. FIG. 5 is a graph in which the y-axis shows concentration of platelet-derived growth factor and the x-axis shows various tested samples. A control of platelet rich plasma that was not activated and a control of whole blood are shown relative to results of exposure of the platelet sample to thrombin and relative to platelets activated with long electric field pulses.

Figure 6:
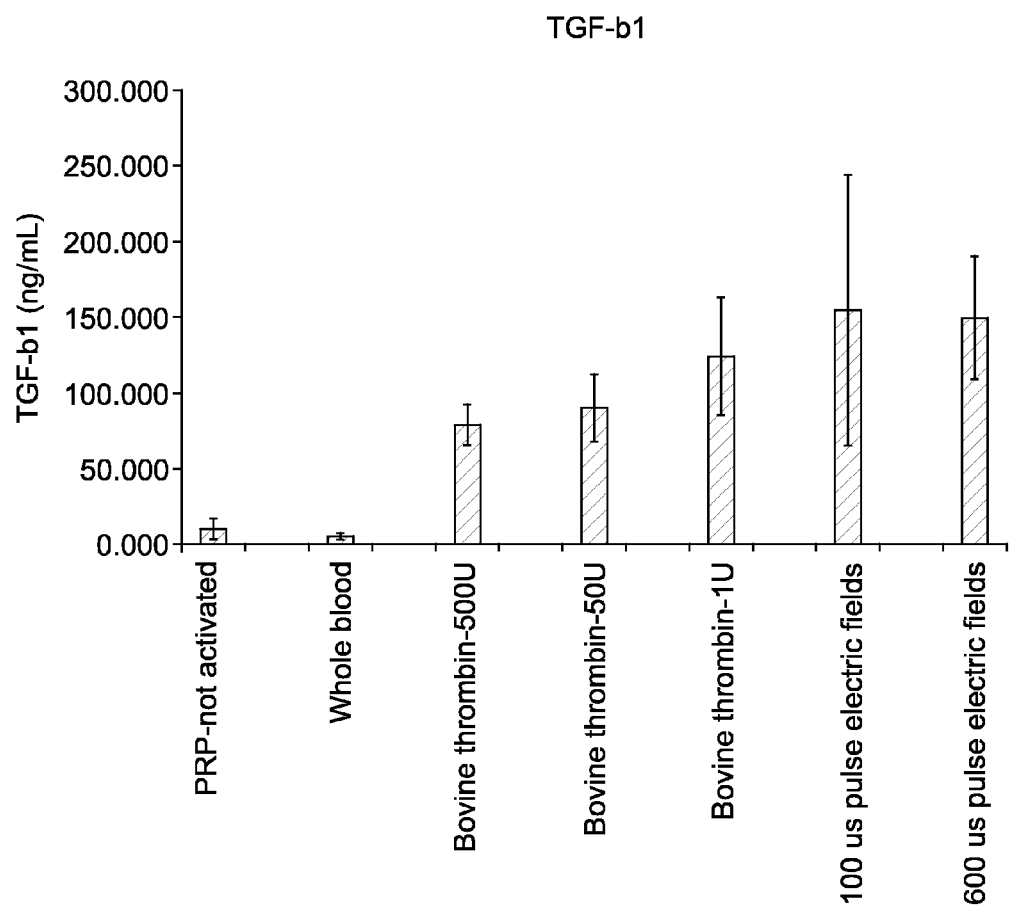
FIG. 6 is a graph showing transforming growth factor-beta 1 release as a marker for platelet activation using various techniques relative to extended duration electric pulses.
Figure 7:
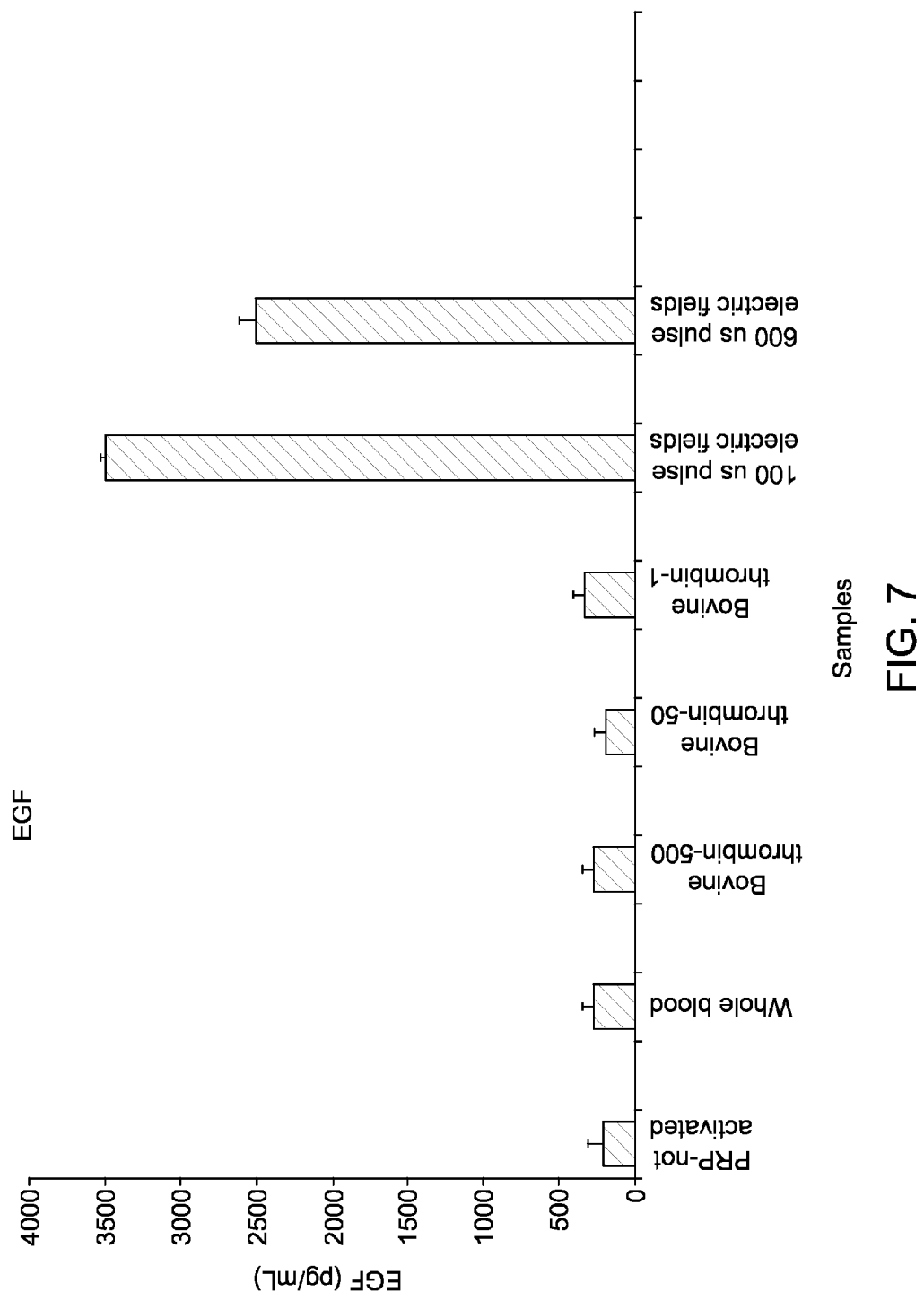
FIG. 7 is a graph showing epidermal growth factor release as a marker for platelet activation using various techniques relative to long electric pulses.

FIG. 6 is a graph showing transforming growth factor-beta1 release for long electric field pulses. Controls and other techniques were also tested. FIG. 7 shows concentration of epidermal growth factor for various tested samples, including a control of platelet rich plasma that was not activated and a control of whole blood. The long electric pulse technique yielded release of epidermal growth factor.

Figure 8:
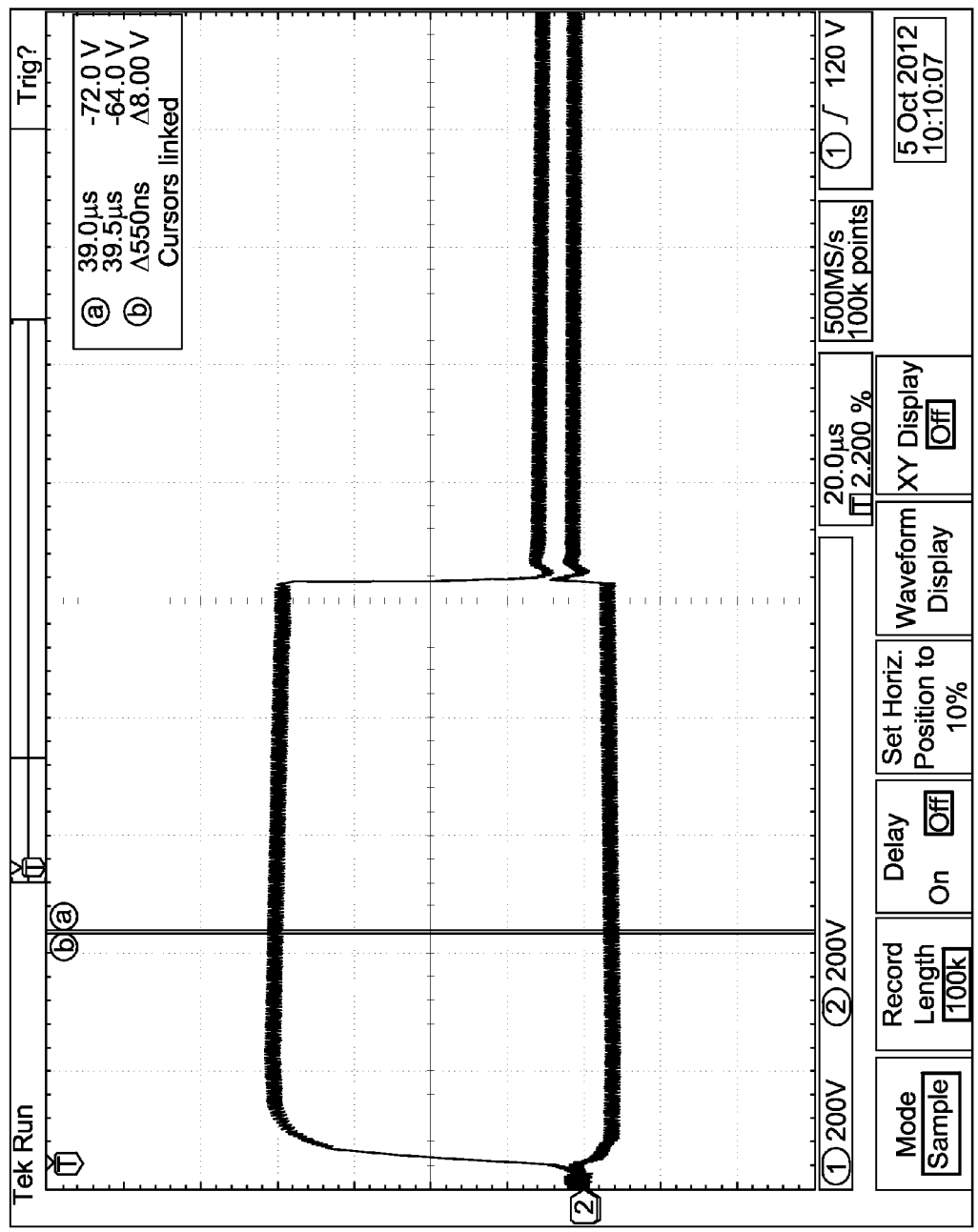
FIG. 8 is an example of an extended duration electric pulse used for platelet activation.
Figure 9:
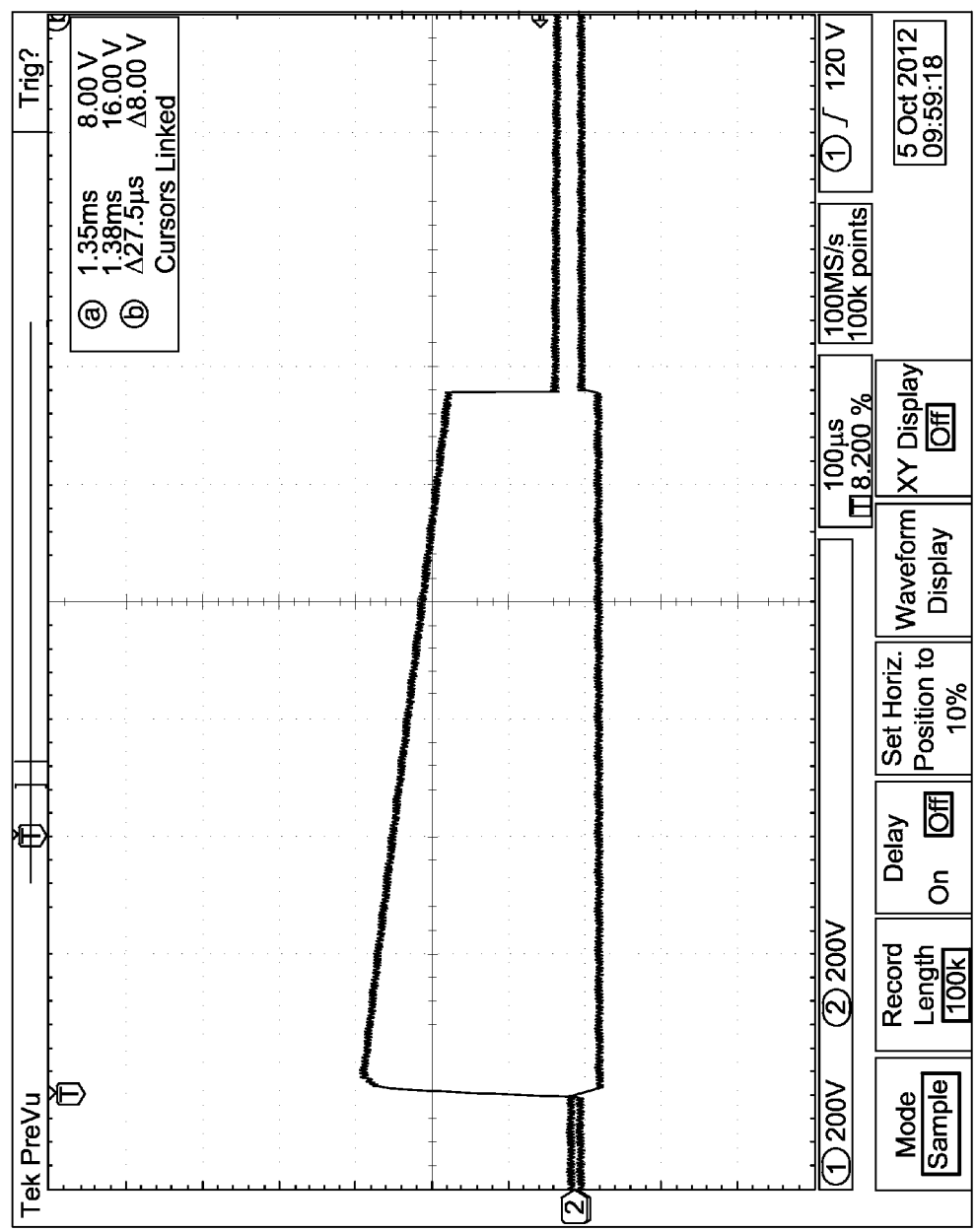
FIG. 9 is a detail view of the pulse of FIG. 8 showing a rise time.
Figure 10:
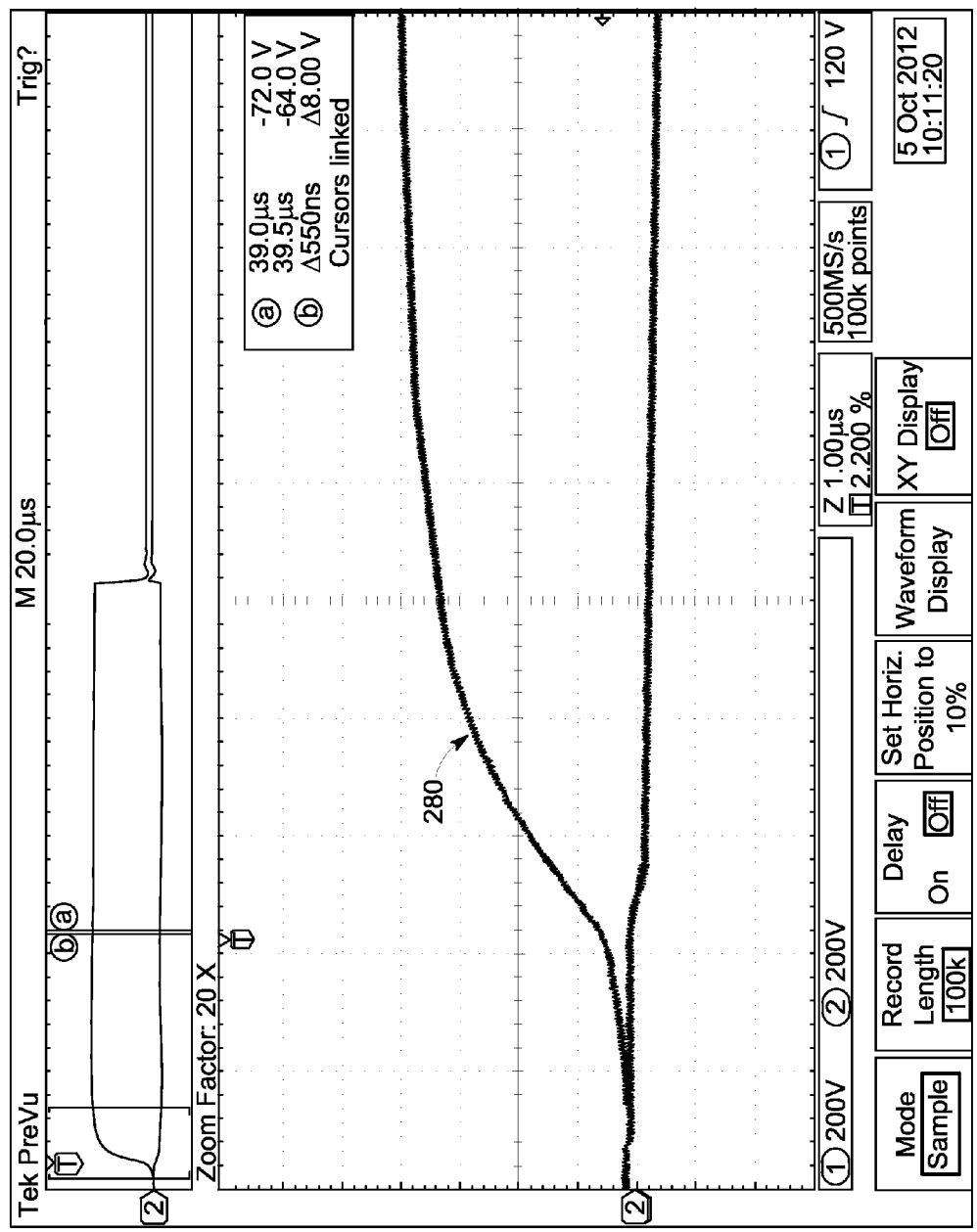
FIG. 10 is a an example of an extended duration electric pulse used for platelet activation.

FIG. 8 is an example of an amplitude profile of a long electric field pulse used for platelet activation (a 100 microsecond pulse at 900V). FIG. 10 is a detail view showing that, although the pulse is generally a rounded wave, the rise 280 of the pulse to full amplitude takes about 7 microseconds for a 100 microsecond pulse at 900V. Because the rise is relatively slower compared to a submicrosecond pulse (that is, the 7 microsecond rise is several times longer than the total pulse length of a submicrosecond pulse), the cuvette 24 (see FIG. 1) may be subject to reduced arcing or electrical discharge that may harm the platelets. Coupled with the lower electric field strength, the risk of arcing is further reduced. Accordingly, the disclosed techniques provide high levels of platelet activation with the potential for improved platelet viability. FIG. 9 is an example of an amplitude profile of a 600 microsecond long electric field pulse used for platelet activation.

As discussed herein, the system 10 may be configured to provide electric pulses longer than 1 microsecond. Accordingly, the disclosed pulse wave shapes and patterns may be implemented as pulses of greater than 1 microsecond. Further, in certain embodiments, at least certain portions of the disclosed pulses may be less than 10 kV. FIGS. 11-21 show examples of pulses and/or pulse patterns that may be generated by the electric field generator 12 and applied to a sample to activated platelets.

Figure 11:
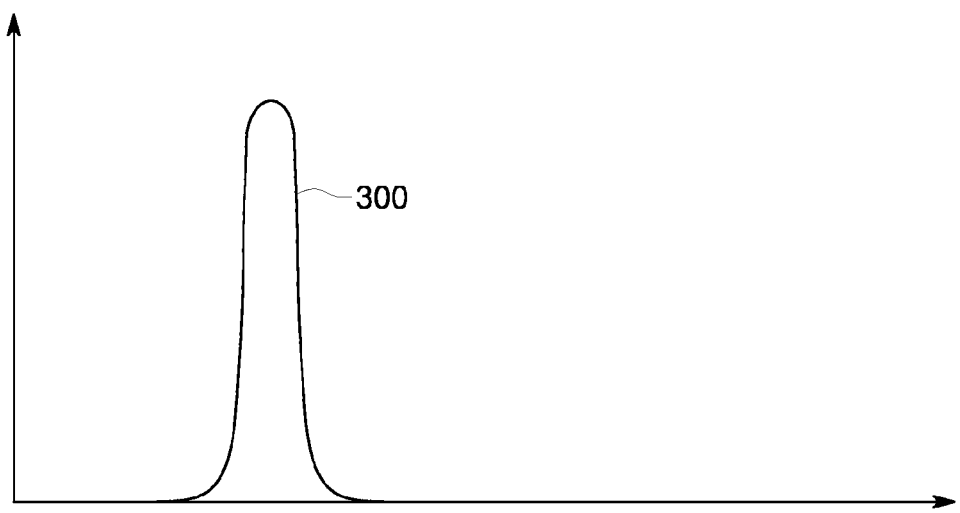
FIG. 11 is an example of an electric pulse that may be used in an embodiment of the present disclosure.
Figure 12:
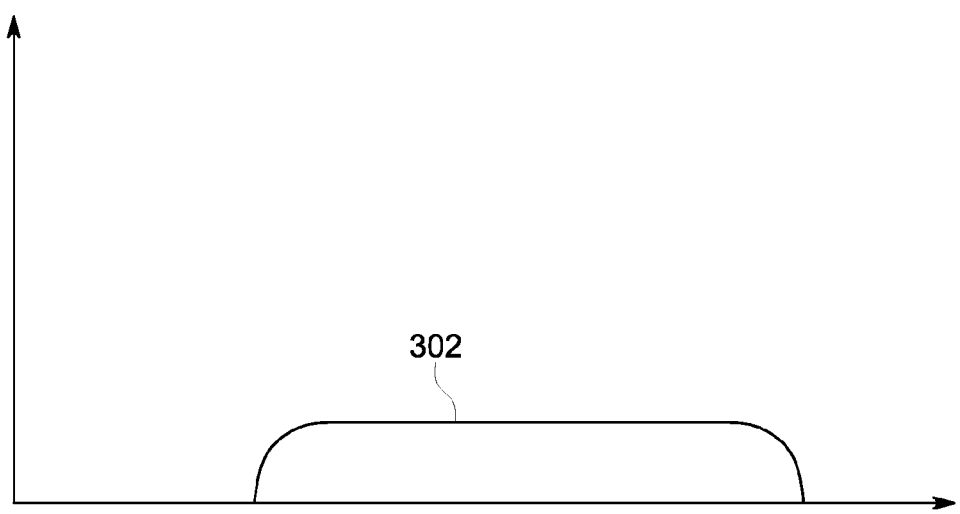
FIG. 12 is an example of an electric pulse that may be used in an embodiment of the present disclosure.

The pulses applied by the system 10 may have different combinations of amplitude and duration depending on the implementation. FIG. 11 is a pulse with a higher amplitude and shorter pulse length than the pulse 302 shown in FIG. 12.

Figure 13:
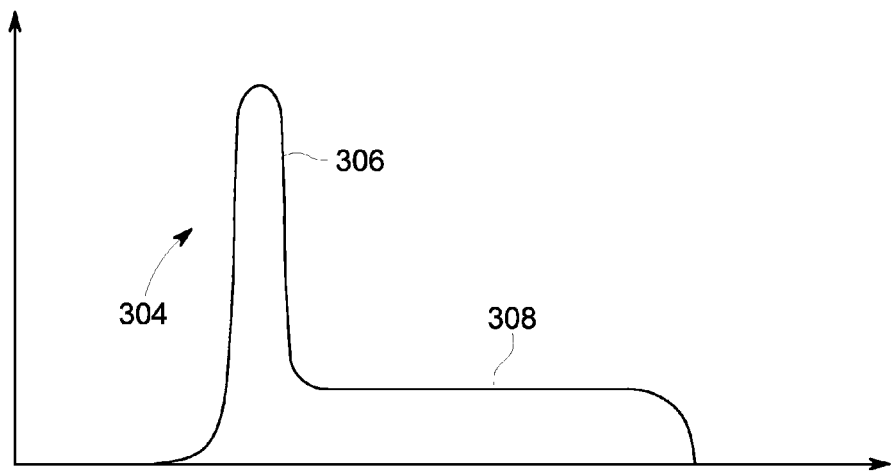
FIG. 13 is an example of an electric pulse consisting of both a high and low electric field component that may be used in an embodiment of the present disclosure.
Figure 14:
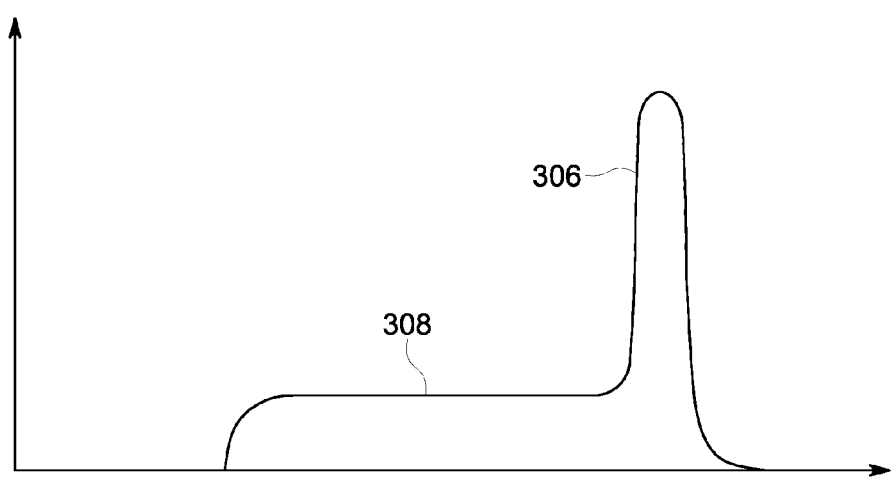
FIG. 14 is an example of an electric pulse consisting of both a high and low electric field component that may be used in an embodiment of the present disclosure.

Square pulses are also contemplated. Different amplitudes and pulse durations may affect different parts of the cell to influence growth factor release and platelet aggregation. FIG. 13 is an embodiment where a pulse 304 has a higher amplitude and shorter duration portion 306 and a lower amplitude, longer duration portion 308. The pulse 304 has a variable shape. In certain embodiments, the higher amplitude, shorter duration portion 306 may target the organelles while the lower amplitude, longer duration portion 308 may affect the cell membrane to facilitate exit of the released growth factors from the cell. In a particular embodiment, the higher amplitude, shorter duration portion 306 is 1 microsecond to approximately 30 microseconds and the lower amplitude, longer duration portion 308 is 99 microsecond to approximately 70 microseconds. Further, the higher amplitude, shorter duration portion 306 may have an amplitude that is at least twice the amplitude of the lower amplitude, longer duration portion 308. FIG. 14 is an embodiment in which the lower amplitude, longer duration portion 308 is the first part of the pulse 310 and the higher amplitude, shorter duration portion 306 is the second part of the pulse 310.

Figure 15:
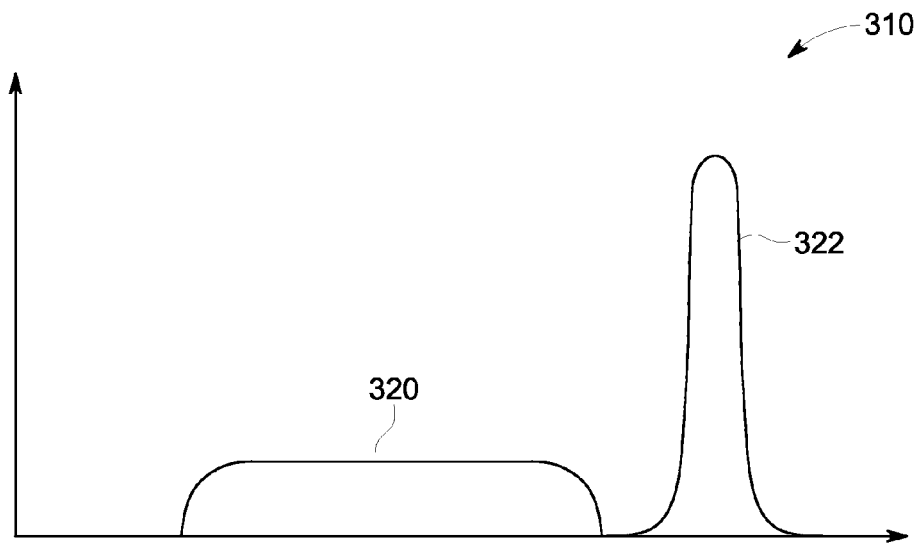
FIG. 15 is an example of a series of electric pulses of different field strengths that may be used in an embodiment of the present disclosure.
Figure 16:
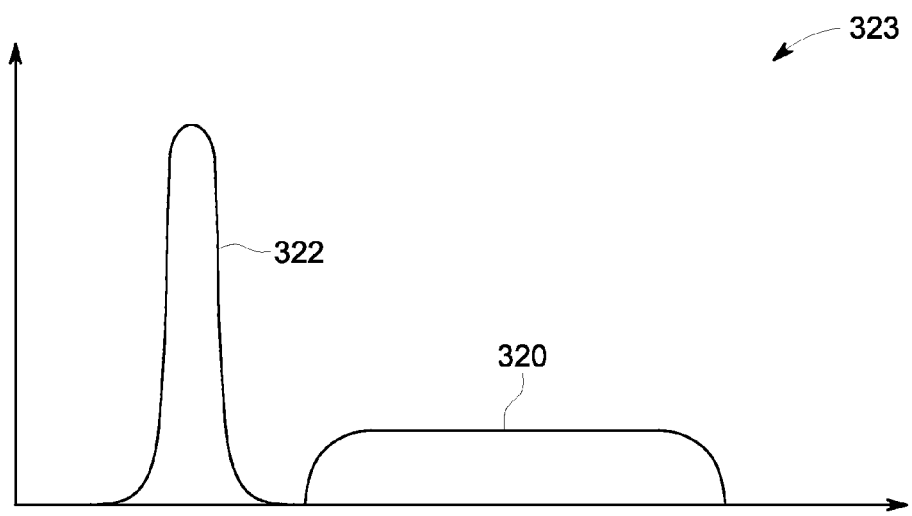
FIG. 16 is an example of a series of electric pulses of different field strengths that may be used in an embodiment of the present disclosure.
Figure 17:
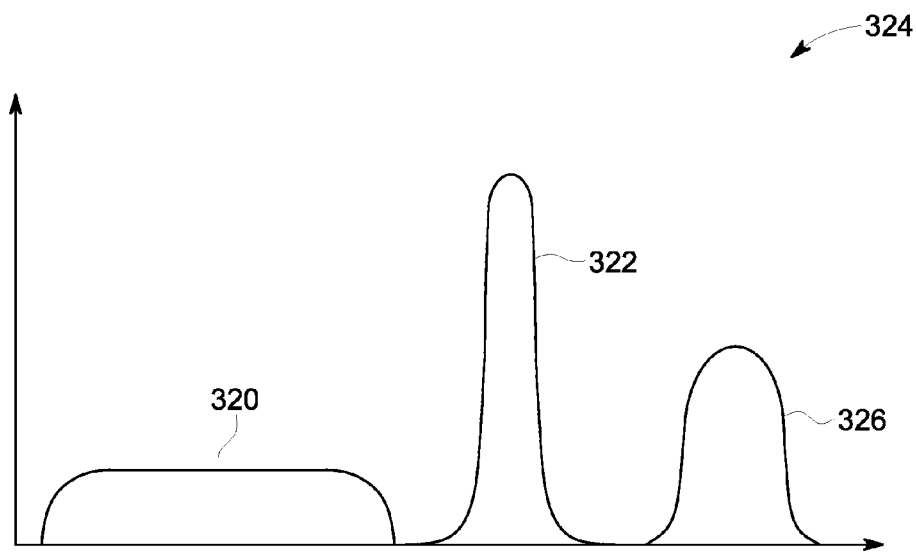
FIG. 17 is an example of a series of electric pulses of multiple field strengths and durations that may be used in an embodiment of the present disclosure.
Figure 18:
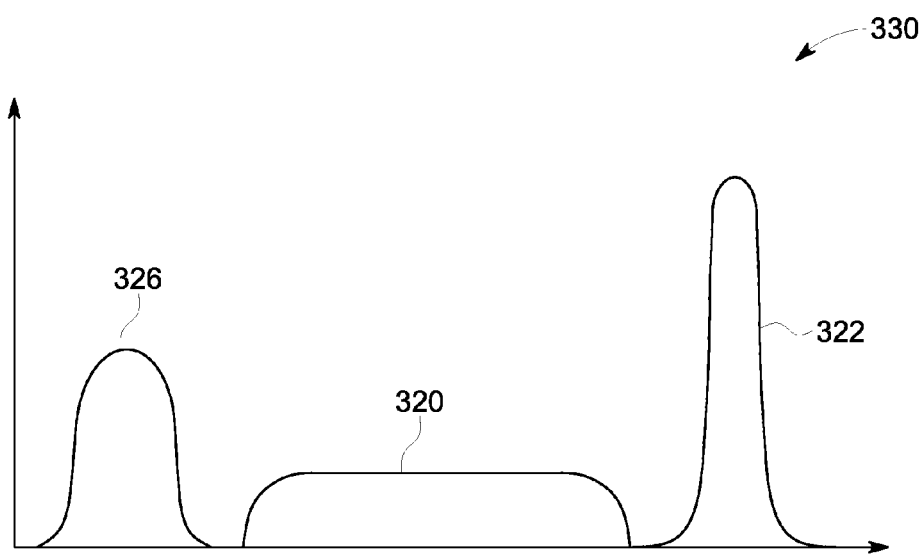
FIG. 18 is an example of a series of electric pulses of multiple field strengths and durations that may be used in an embodiment of the present disclosure.

FIGS. 15-18 show different pattern combinations of pulses. For example, FIG. 15 is an example of a pulse pattern 310 with a lower amplitude, longer duration pulse 320 followed by a higher amplitude, shorter duration pulse 322. FIG. 16 shows a pattern 323 in which the arrangement between the pulses 320 and 322 is reversed. For a repeating pulse pattern, the effects of the patterns 310 and 320 may be similar. FIG. 17 shows a pattern 324 in which a pulse 326 of amplitude and duration between those of the pulses 320 and 322 is part of the pattern. FIG. 18 shows an example of a different pattern 330 in which the medium amplitude and duration pulse 326 is arranged as the first pulse in the pattern 330.

Figure 19:
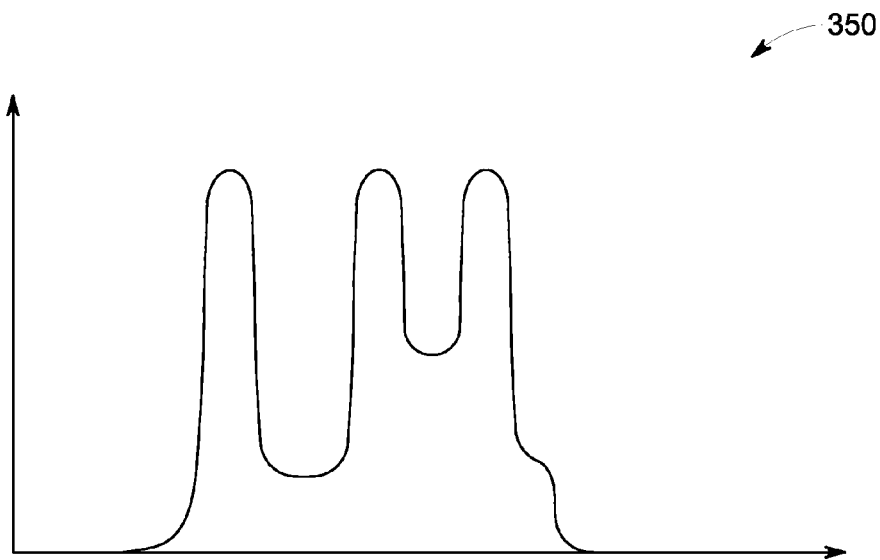
FIG. 19 is an example of a pulse train consisting of pulses of variable duration and amplitude that may be used in an embodiment of the present disclosure.
Figure 20:
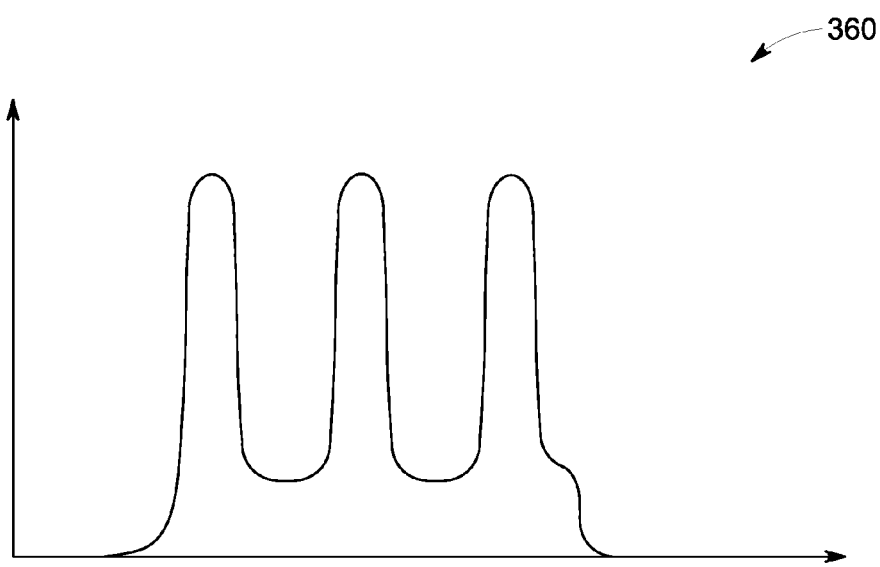
FIG. 20 is an example of a pulse train consisting of pulses of variable duration and amplitude that may be used in an embodiment of the present disclosure.
Figure 21:
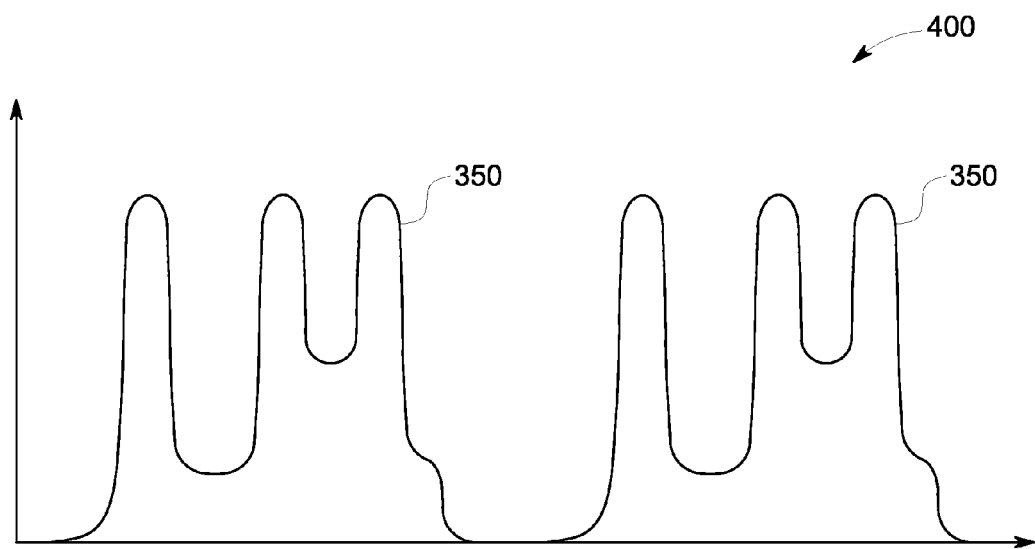
FIG. 21 is an example of a series of pulses of variable duration and amplitude that may be used in an embodiment of the present disclosure.
Figure 22:
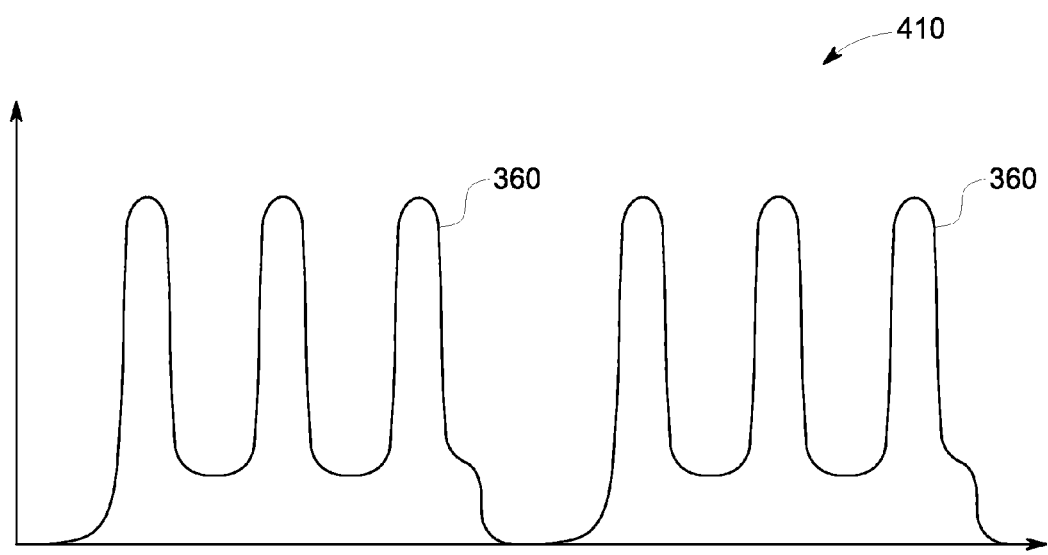
FIG. 22 is an example of a series of pulses of variable duration and amplitude that may be used in an embodiment of the present disclosure.

It is also contemplated that the pulses may include shaped patterns within each pulse. For example, FIG. 19 shows an example of a pulse 350 with higher amplitude portions, lower amplitude portions, and medium amplitude portions. FIG. 20 shows an example of a pulse 360 with alternating high and low amplitude portions. FIG. 21 is a pattern 400 formed from a series of pulses 350, and FIG. 22 is a pattern 410 formed from a series of pulses 360. Further, it is contemplated that pulse patterns may include combinations of different types of shapes pulses, such as pulses 350 and 360.

Technical effects include activating platelets for wound healing or hemostasis. The disclosed techniques provide a reliable method of activating platelets while reducing the risk of arcing by using longer pulses with lower electric field strength.

This written description uses examples to disclose features of the embodiments, including the best mode, and also to enable any person skilled in the art to practice the disclosure, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method of activating platelets, comprising:
   exposing a platelet-containing sample to a pulsed electric field comprising at least one pulse, wherein;
   the at least one pulse has a duration of at least 100 microseconds;
   a field strength of 5 kV/cm or less;
   or a combination thereof; and
   applying the platelet-containing sample to a patient.

2. The method of claim 1, wherein the at least one pulse has a variable electric field strength over the course of the pulse.

3. The method of claim 1, wherein a first portion of the at least one pulse has a greater field strength than a second portion.

4. The method of claim 3, wherein the second portion has a longer duration than the first portion.

5. The method of claim 1, wherein the pulsed electric field comprises two or more pulses of different durations.

6. The method of claim 1, wherein the pulsed electric field comprises two or more pulses with different field strengths.

7. The method of claim 1, wherein the platelet-containing sample is autologous blood.

8. The method of claim 1, wherein the platelet-containing sample comprises platelet rich plasma.

9. The method of claim 1, wherein applying the sample to a patient comprises applying a gel formed by exposing the platelet-containing sample to the pulsed electric field.

10. A method of activating platelets, comprising:
    receiving a user input related to a platelet-containing sample; and
    applying one or more electric pulses to the platelet-containing sample based on the user input, wherein;
    at least one pulse has a duration of at least 100 microseconds;
    a field strength of 5 kV/cm or less;
    or a combination thereof.

11. The method of claim 10, wherein the user input comprises input related to a pulse shape.

12. The method of claim 10, wherein the user input comprises input related to a total duration of the one or more pulses.

13. The method of claim 10, comprising selecting a protocol from a plurality of protocols stored in a memory based on the user input, wherein executing the protocol results in applying the one or more electric pulses.

* * * * *